United States Patent [19]

Bertolini et al.

[11] 4,123,471

[45] Oct. 31, 1978

[54] OLEFIN PRODUCTION PROCESS

[76] Inventors: Natale Bertolini, via G.A. Amedeo 54, Milan; Claudio Divo, via Ramazzotti 20, Saronno (Varese); Petri Maris, via C. Battisti 23/A, Paderno Dugnano (Milan); Giovanni Maiorano, via Assietta 31, Milan, all of Italy

[21] Appl. No.: 819,613

[22] Filed: Jul. 26, 1977

[51] Int. Cl.$^2$ .............................................. C07C 3/16
[52] U.S. Cl. ........................................... 260/683.15 C
[58] Field of Search .............. 260/683.15 R, 683.15 C

[56] References Cited

U.S. PATENT DOCUMENTS

| | | | |
|---|---|---|---|
| 2,182,617 | 12/1939 | Michel et al. | 260/683.15 C |
| 2,728,804 | 12/1955 | Mueller | 260/683.15 C |
| 3,658,936 | 4/1972 | Erdmann | 260/683.15 C |

FOREIGN PATENT DOCUMENTS 859,491  2/1970  Italy.

OTHER PUBLICATIONS

Langlois et al., Third World Petroleum Congress Proceedings, Sect. IV, 1951, pp. 191-200.
Egloff et al., Third World Petroleum Congress Proceedings, Sect. IV, 1951, pp. 201-214.

*Primary Examiner*—C. Davis

[57] ABSTRACT

This invention describes a process for producing branched $C_7$-$C_9$-mono-olefins by polymerizing a mixture of propylene and butenes over phosphoric acid catalysts at temperatures and pressures which ensure a homogeneous liquid phase and recycling the fraction containing over $C_9$ olefins.

14 Claims, No Drawings

OLEFIN PRODUCTION PROCESS

This invention relates to an improved process for producing branched mono-olefins with 7 to 9 carbon atoms ($C_7$-$C_9$ olefins) by polymerizing a mixture of propylene and butenes over phosphoric acid-based catalysts.

It is known technically to produce $C_7$-$C_9$ olefins by the contact of propylene and butenes with phosphoric acid catalysts supported on silica, the operation being carried out at high temperature and pressure.

In particular, in said known processes the gaseous reagents are fed to the top of a long vertical reactor and flow through the catalyst arranged in the form of a fixed bed or several fixed beds in succession.

The products leaving the bottom are then fractionated.

The feed to the reactor may be either pure propylene and butenes, or gaseous mixtures containing propylene and butenes originating from the thermal or catalytic cracking of suitable petroleum fractions or thermal reforming.

The catalysts suitable for this purpose are known technically and are prepared by impregnating a silica or silica-containing support with phosphoric acids, and then calcining the support after impregnation. The main problems encountered in the production of $C_7$-$C_9$ olefins are problems related to the control of the progress of the strongly exothermic reaction, and problems deriving from the distribution of the reaction products.

In order to control the heat development, it is usual to dilute the gaseous feed stream with non-reactive substances, generally hydrocarbons such as propane or butane.

These cold non-reactive substances may be fed at one or more points along the catalyst bed.

Alternatively, or in addition to this arrangement, the reactor may be provided with suitable heat transfer surfaces in order to extract the evolved heat, e.g. by using reactors in the form of a tube bundle, or reactors provided with coils or the like.

In spite of these arrangements, there is frequently rapid de-activation of the catalyst due to the deposition of tarry products, and disintegration of the catalyst particles.

These phenomena are considered to be at least partly a consequence of the formation of "hot points" in the catalyst bed, at which the reaction proceeds in an uncontrollable manner.

This variation in catalytic activity in any case creates considerable difficulty in the operation of industrial plants.

The polymerization of propylene and butenes in accordance with the known art gives olefin mixtures of a wide range of composition, generally from 6 to about 15 carbon atoms.

$C_6$ olefins and olefins beyond $C_9$ are used in the fuel sector.

The $C_7$-$C_9$ fraction is used as a raw material in the preparation of oxo-alcohols and is the most interesting fraction from the application aspect.

There is therefore a certain interest in improving the yield of the $C_7$-$C_9$ olefin fraction at the expense of the other reaction products, bearing in mind that when operating in accordance with the known art, an average of 0.5-0.7 Kg of $C_7$-$C_9$ olefins are produced for each Kg of propylene and butenes converted.

It is also of interest to provide a process which, besides giving a high yield of $C_7$-$C_9$ olefins, also enables the ratio of the constituents of said fraction to be varied over a wide range in accordance with particular market requirements.

In this respect, known processes are not sufficiently flexible to allow any particular olefin to prevail in the production.

The disadvantages of the prior art are obviated according to the present invention by a process for polymerizing propylene and butenes in the homogeneous liquid phase which on the one hand enables the formation of olefins beyond $C_9$ to be reduced or even eliminated, and on the other hand enables the polymerization to be controlled so that the formation of any one particular olefin in the range containing 7 to 9 carbon atoms prevails.

Operation in the homogeneous liquid phase considerably reduces the de-activation phenomena deriving from the deposition of tar on the catalyst and the formation of hot points in the catalyst bed. More particularly, the present invention relates to a process for preparing $C_7$-$C_9$ olefins from a mixture of propylene and butenes over supported phosphoric acid catalysts, said process being characterized in that:

a stream comprising propylene, butenes and recycle olefins beyond $C_9$ are fed to one end of an adiabatic reaction zone containing the catalyst (in this specification "adiabatic reaction zone" means a reaction zone wherein no substantial heat transfer occurs);

the operation is carried out in said zone at a temperature of 160° to 300° C. and under pressure such as to maintain the reagents and reaction products in the homogeneous liquid phase, until at least 30% but not more than 70% of the fed propylene and butenes has been converted;

the reaction products are recovered at the other end of the reaction zone, and the unaltered propylene and butenes, the $C_6$ olefins, the $C_7$-$C_9$ fraction and the fraction beyond $C_9$ are separated;

the latter fraction is wholly or at least partially recycled to that end of the reaction zone to which the reagents are fed, and if required the unaltered propylene and butenes are fed to the same end.

Thus one characteristic of the process according to the present invention is the polymerization of the propylene and butenes in the homogeneous liquid phase (i.e., in the complete or substantially complete absence of the gaseous phase), the homogeneous liquid phase being guaranteed by recycling the olefins beyond $C_9$ which constitute one of the reaction products.

Such a method of operation firstly leads to better utilization of the catalyst by its being continuously wetted by the liquid phase, with consequent removal of the tar which would otherwise deposit on its surface.

Furthermore, with the homogeneous liquid phase there is no formation of preferential paths in the catalyst bed, which are frequent in the case of a mixed liquid-gas phase and which create hot points and the uncontrollable development of the polymerization reaction. It has also been found that the quantity of olefins beyond $C_9$ produced in the reaction is not only related to the degree of conversion of the fed propylene and butenes but also depends on the presence of said heavy olefins in the feed flow in the reaction zone.

In other words, the net formation of olefins beyond $C_9$ is lower the lower the degree of conversion of the reagents and the higher the quantity of heavy olefins fed together with the reagents.

Thus in accordance with a further characteristic of the process according to the invention, the olefins beyond $C_9$ are recycled to prevent their accumulation in the reaction products, or at least to control said accumulation within a required range of values.

It has also been found that the amount of the recycle stream, or rather the ratio of the recycle stream to the fed propylene and butenes influences the distribution of the $C_7$–$C_9$ olefins. Thus in accordance with a further characteristic of the process according to the present invention, the yield may be modified towards one or the other of the olefins by simply varying the parameters, including said ratio.

In the description given hereinafter, $C_6$ olefins signify those reaction products which boil at 20° to 80° C.;

$C_7$–$C_9$ olefins signify those which boil at over 80° C. and up to 145° C.;

olefins beyond $C_9$ signify those which boil beyond 145° C.

Furthermore, in the $C_7$–$C_9$ olefin range:

heptenes signify those products which boil over 80° C. and up to 100° C.;

octenes are those which boil at over 100° C. and up to 125° C.;

nonenes are those which boil at over 125° C. and up to 145° C.

Thus in the process according to the present invention, a stream containing propylene, butenes and recycle olefins beyond $C_9$ is fed to one end of a reaction zone containing the phosphoric acid-based supported catalyst.

The catalysts useful for this purpose are those known catalysts prepared by mixing phosphoric acids with a siliceous support and then subjecting the impregnated support to heat treatment.

Supports suitable for the purpose are silica, and preferably diatomite containing more than about 80% by weight of silica.

The phosphoric acids which may be used include orthophosphoric, metaphosphoric and/or pyrophosphoric acid, and generally acids in which the valency of the phosphorus is 5.

The best results are obtained by those phosphoric acids with a high $P_2O_5/H_2O$ ratio, for example the product known as polyphosphoric acid, the $P_2O_5$ content of which is about 85% by weight.

The catalyst is prepared in the usual manner by reducing the impregnated support to granules, followed by drying and calcining. This latter operation is usually conducted at a temperature of 200° to 900° C. and preferably 250° to 600° C., generally by gradually raising the temperature to the chosen value.

In all cases, the catalysts preferred for the present invention are those which contain in the order of 65% by weight of phosphorus expressed as $P_2O_5$.

Said catalysts are disposed in the form of a fixed bed in the polymerization reactor, and the feed stream is fed to the head, or preferably to the foot of the reactor.

In said stream, the weight ratio of the propylene to butenes may vary between wide limits such as 0.3/1 to 3/1, the preferred value being of the order of 1/1.

The term butenes signifies isobutene, butene-1, butene-2 or mixtures thereof.

Generally use is made of the already mentioned olefin fractions originating from petroleum refining operations, which contain all the aforementioned constituents.

In this case the mixture fed to the reactor also contains hydrocarbons which are inert under the conditions of operation, these being essentially propane and butanes.

As a special characteristic of the invention is to only partially convert the propylene and butenes in each passage and then recycle the unconverted part after partial purging, usually the operation is carried out with the weight ratio of said saturated hydrocarbons to the propylene and butenes of less than 5/1, and generally of the order of 1/1.

The quantity of olefins beyond $C_9$ for recycle must be at least equal to the quantity required to guarantee the homogeneous liquid phase under polymerization conditions.

Thus the minimum weight ratio of said recycle stream to the propylene and butenes is of the order of 2/1 to 3/1.

If the amount of saturated hydrocarbons present is high, then the value of this latter ratio is proportionally increased.

Higher values of said ratio are used when operating at higher temperature or lower pressure, bearing in mind the need to maintain a homogeneous liquid phase under reaction conditions.

If a small increase in temperature between the inlet and outlet of the reaction zone is required for the same degree of conversion of the reagents, the ratio of olefins beyond $C_9$ to the propylene and butenes should be high.

The maximum value of this ratio depends on economical considerations.

It has also been found desirable for water to be present in the feed stream to the reactor, normally its quantity being maintained at around 500–2,000 ppm.

The polymerization temperature may vary over a wide range such as 160° to 300° C., preferably 180° to 250° C.

The pressure used for this purpose may vary over a wide range such as 10 to 60 $Kg/cm^2$, the particular value depending upon the composition of the feed stream and other operational conditions, so as to guarantee the homogeneous liquid phase in the reaction zone.

Thus typically with a weight ratio of reagents and possible inerts to olefins beyond $C_9$ of the other of 0.33/1 and a polymerization temperature of 200°–250° C., the pressure used to maintain the homogeneous liquid phase is around 40 $kg/cm^2$.

It is also convenient to pre-heat the feed stream to the reactor to a temperature of 160° to 240° C.

The reaction does not begin below 160° C., while above 240° C. the exothermic nature of the reaction means that the temperature reached is such as to cause rapid deactivation of the catalyst. According to the present invention, the propylene and butenes are only partially converted, and generally this conversion may vary from 30 to 70%, the preferred value being of the order of 50%. The conversion may be influenced by choice of temperature, by adjusting the residence time under polymerization conditions and by varying the ratio of olefins beyond $C_9$ to the propylene and butenes, bearing in mind that the reaction velocity is reduced by a higher dilution of the reagents.

Given the temperature of the operation, said residence time may vary from 10 to 60 minutes, calculated as the ratio of the catalyst volume to the feed volume per minute, said feed being considered liquid at ambient temperature.

In a preferred embodiment of the process according to the present invention, a number of separate adiabatic catalyst beds are used disposed in series, feeding the whole of the propylene and butene reagents to the first bed together with the olefins beyond $C_9$ in the ratio previously indicated.

A further quantity of olefines beyond $C_9$ is generally fed at ambient temperature between each pair of adjacent beds in order to control the exothermic extent of the reaction.

The number of catalyst beds may vary from 2 to 10, preferably from 3 to 5, and in each case said number depends on the maximum temperature difference to be maintained between the oulet and inlet stream for each individual bed.

Conveniently this temperature difference is 1° to 70° C., preferably 5° to 25° C.

Under these conditions the purpose of the olefins beyond $C_9$ recycled between one stage and another is to cool the reaction mixture leaving each catalyst bed, this cooling conveniently proceeding to a temperature equal or approximately equal to the inlet temperature to the catalyst bed.

It is evidently possible to control the temperature and quantity of the olefins beyond $C_9$ between adjacent stages so as to obtain the required temperature profile at each individual stage.

The mixture leaving the polymerization reactor, or leaving the last catalyst bed in the case of a number of reaction stages, contains unconverted propylene and butenes and possibly inert saturated hydrocarbons, in addition to $C_9$–$C_{15}$ branch olefins. The mixture is fed to a distillation section where the following are separated out:

propylene and butenes, and any propane and butanes, which are generally recycled after purging to prevent accumulation of inerts;
the $C_6$ fraction, used in gasoline;
the $C_7$–$C_9$ fraction which is collected and used for the production of oxo-alcohols;
the fraction beyond $C_9$, which is wholly or partially recycled.

As previously stated, the extent of this recycling is controlled in relation to the provision of a homogeneous liquid phase during polymerization, the degree of accumulation of olefins beyond $C_9$ and the amount of cooling of the reaction mixture when using a number of catalyst beds in series.

By means of the process according to the present invention, it is possible to influence the reaction towards the prevalent formation of a specific olefin in the range $C_7$ to $C_9$.

For this purpose, the polymerization temperature, the conversion undergone by the propylene and butenes during each passage and the ratio of these reagents may be varied in addition to the ratio of the olefin beyond $C_9$ to the propylene and butenes.

Thus, other conditions being equal, a lower reagent conversion favors the formation of $C_7$ olefins, while a higher propylene/butene ratio favors a higher $C_9$ olefin yield.

Finally, a higher polymerization temperature, other conditions being equal, favors the formation of $C_7$ olefins.

In all cases reaction products are obtained with a mono-olefin content exceeding 98% (ASTM D-13-19), and said olefins are particularly suitable for the production of oxo-alcohols.

EXAMPLE 1

Three adiabatic reactors are used in series containing a total of 70 Kg (approximately 72 liters) of the catalyst in the form of a fixed bed.

The catalyst consists of phosphoric acids mainly supported on diatomite, and has a $P_2O_5$ content of 65% by weight.

205 Kg/hour of a liquid mixture preheated to 200° C. is fed to the bottom of the first reactor, and has the following average composition:

| propylene | 6.25% by weight |
| butenes | 6.25% by weight |
| propane and butanes | 12.50% by weight |
| olefins beyond $C_9$ | 75.00% by weight |

The feed stream also contains a quantity of water equivalent to the saturation value at ambient temperature.

The reaction products discharged from the top of each reactor are fed to the bottom of the next reactor after adding 18.5 Kg/hour of olefins beyond $C_9$ between the first and second reactor and 13.3 Kg/hour of olefins beyond $C_9$ between the second and third reactor.

The olefin hydrocarbons containing 3 and 4 carbon atoms fed to the first reactor form the fresh portion (60%) of the feed, with the remainder being the recycle from the distillation section.

The olefins beyond $C_9$ fed to the three reactors are the recycle olefins from said distillation section.

In the first reactor the operating pressure is approximately 41 Kg/cm$^2$, and the products discharged from the top at a temperature of 215° C. are cooled to 200° C. by the stream of olefins beyond $C_9$, and are then fed to the bottom of the second reactor.

In the second reactor, the operating pressure is approximately 40 Kg/cm$^2$, and the products discharged from the top at a temperature of 210° C. are cooled to 200° C. by injecting olefines beyond $C_9$, and are then fed to the bottom of the third reactor.

In the third reactor, the operating pressure is about 39 Kg/cm$^2$, and the overall conversion of the propylene and butenes in the three reactors is in the order of 45.0%.

The products discharged from the top of the third reactor at a temperature of 205° C. are fed to a column operating at 10 Kg/cm$^2$ where approximately 40 Kg/hour of a hydrocarbon mixture containing unaltered propylene and butenes plus propane and butanes separates from the top.

This mixture is recycled to the first catalyst bed after partially purging in order to maintain the concentration of saturated hydrocarbons constant.

Approximately 197 Kg/hour of an olefin mixture are recovered from the bottom of the column, the mixture having the following average composition:

| $C_6$ fraction | 12.0% by weight |
| $C_7$ fraction | 41.5% by weight |
| $C_8$ fraction | 16.5% by weight |
| $C_9$ fraction | 27.0% by weight |
| fraction beyond $C_9$ | 3.0% by weight |

The mixture is distilled to separate the $C_6$ fraction (1.38 Kg/hour), the $C_7$ fraction (4.79 Kg/hour), the $C_8$ fraction (1.50 Kg/hour) and the $C_9$ fraction (1.11 Kg/hour).

The residue from said distillation (approximately 197 Kg/hour) is almost totally recycled, and the net production of olefins beyond $C_9$ is approximately 0.35 Kg/hour.

EXAMPLES 2-8

The operation is carried out in a like manner to example 1, but varying the composition of the feed stream to the first reactor and/or the degree of overall conversion of the propylene and butenes. Furthermore, in examples 4,5 and 6, the temperature of the streams entering the reactors is 220° C. instead of 200 as in the other cases. The results of these examples are shown in table 1.

Table 1

| Feed (% by weight) | Ex.2 | Ex.3 | Ex.4 | Ex.5 | Ex.6 | Ex.7 | Ex.8 |
|---|---|---|---|---|---|---|---|
| propylene | 6.25 | 6.25 | 6.25 | 6.25 | 3.75 | 5.0 | 8.3 |
| butenes | 6.25 | 6.25 | 6.25 | 6.25 | 3.75 | 7.5 | 4.2 |
| propane and butanes | 12.50 | 12.50 | 12.50 | 12.50 | 17.5 | 12.5 | 12.5 |
| olefins beyond $C_9$ | 75.00 | 75.00 | 75.00 | 75.00 | 75.0 | 75.0 | 75.0 |
| Residence time (mins.) | 20 | 38 | 12 | 21 | 15 | 22 | 19 |
| Reactor inlet temperature (° C) | 200 | 200 | 220 | 220 | 220 | 200 | 200 |
| Conversion (% by weight) | 51.0 | 62.0 | 46.0 | 64.6 | 43.0 | 52 | 49 |
| Yield on converted product (% by weight) | | | | | | | |
| $C_6$ olefins | 9.5 | 7.0 | 12.5 | 7.0 | 13.0 | 6.0 | 11.0 |
| $C_7$ olefins | 37.0 | 30.0 | 45.0 | 33.5 | 46.0 | 31.0 | 30.0 |
| $C_8$ olefins | 15.0 | 13.0 | 19.5 | 18.5 | 19.5 | 28.0 | 8.0 |
| $C_9$ olefins | 24.5 | 20.0 | 21.5 | 18.5 | 20.5 | 18.0 | 35.0 |
| olefins beyond $C_9$ | 14.0 | 30.0 | 1.5 | 22.5 | 1.0 | 17.0 | 16.0 |

We claim:

1. A process for preparing $C_7$-$C_9$ olefins from a mixture of propylene and butenes, over a supported phosphoric acid catalyst, comprising the steps of
    feeding a stream comprising propylene, butenes and recycle olefins beyond $C_9$ to one end of an adiabatic reaction zone containing the catalyst;
    carrying out the operation in said zone at a temperature of 160° to 300° C. and under a pressure such as to maintain the reagents and reaction products in the homogeneous liquid phase, until at least 30% but not more than 70% of the fed propylene and butenes has been converted;
    recovering the reaction products at the other end of the reaction zone, and separating the unconverted propylene and butenes, the $C_6$ olefins, the $C_7$-$C_9$ fraction and the fraction beyond $C_9$
    and at least partially recycling the latter fraction to that end of the reaction zone to which the reagents are fed.

2. The process of claim 1 wherein the weight ratio of the propylene to the butenes fed to the reaction zone is 0.3/1 to 3/1.

3. The process of claim 1, wherein the feed stream to the reaction zone contains saturated hydrocarbons, the weight ratio of said saturated hydrocarbons to the propylene and butenes being less than 5/1.

4. The process of claim 1, wherein the minimum weight ratio of the olefins beyond $C_9$ to the propylene and butenes in the feed is in the order of 2/1 to 3/1.

5. The process of claim 1, wherein the feed stream to the reaction zone is preheated to a temperature of 160° to 240° C.

6. The process of claim 1, wherein in the reaction zone the operating temperature is 180° to 250° C. and the operating pressure 10 to 60 Kg/cm².

7. The process of claim 1, wherein the conversion of the propylene and butenes in the reaction zone is in the order of 50%.

8. The process of claim 1, wherein the residence time in the reaction zone is 10 to 60 minutes.

9. The process of claim 1, wheren unconverted propylene and butenes are recycled to that end of the reaction zone to which the reagents are fed.

10. The process of claim 3, wherein the saturated hydrocarbons are selected from the group consisting of propane and butanes, the ratio of said saturated hydrocarbons to the propylene and butenes being in the order of 1/1.

11. A process for preparing $C_7$-$C_9$ olefins from a mixture of propylene and butenes over a supported phosphoric acid catalyst comprising the steps of
    feeding a stream comprising propylene, butenes and recycle olefins beyond $C_9$ to the first bed of a series of catalyst beds comprising a series of adiabatic reaction zones;
    feeding a further quantity of olefins beyond $C_9$ between each pair of adjacent beds;
    carrying out the operation in said zones at a temperature of 160° to 300° C. and under a pressure such as to maintain the reagents and reaction products in the homogeneous liquid phase, until at least 30% but not more than 70% of the fed propylene and butenes has been converted;
    recovering the reaction products at the end of the last reaction zone, and separating the unconverted propylene and butenes, the $C_6$ olefins, the $C_7$-$C_9$ olefins and the fraction beyond $C_9$.

12. The process of claim 11, wherein the operation is carried out with 2 to 10 catalyst beds in series, and a temperature difference of 1° to 70° C. is maintained between the outlet stream and inlet stream at each individual bed.

13. The process of claim 12, wherein the number of catalyst beds is 3 to 5 and the temperature difference is 5° to 25° C.

14. The process of claim 2 wherein the weight ratio of the propylene to the butenes fed to the reaction zone is 1/1.

* * * * *